United States Patent [19]
Poucher et al.

[11] Patent Number: 5,287,168
[45] Date of Patent: Feb. 15, 1994

[54] SENSOR FOR MONITORING SOLUTE IN A LIQUID STREAM

[75] Inventors: David Poucher; Chilengi Madhusudhan, both of Torrance; Joaquin M. Otero, Carson, all of Calif.

[73] Assignee: Hughes Aircraft Company, Los Angeles, Calif.

[21] Appl. No.: 72,668

[22] Filed: Jun. 7, 1993

Related U.S. Application Data

[63] Continuation of Ser. No. 785,727, Oct. 31, 1991, abandoned.

[51] Int. Cl.$^5$ ............... G01N 21/53; G01N 21/09
[52] U.S. Cl. ................... 356/436; 356/410; 356/440; 250/573; 250/576
[58] Field of Search ............ 356/436, 410, 440; 250/573, 576

[56] References Cited

U.S. PATENT DOCUMENTS

| | | | |
|---|---|---|---|
| 3,890,510 | 6/1975 | Sturm | 356/436 |
| 4,786,171 | 11/1988 | LeFebre et al. | 356/440 |
| 4,851,665 | 7/1989 | Pesavento et al. | 356/436 |
| 4,917,491 | 4/1990 | Ring et al. | 356/440 |
| 4,989,942 | 2/1991 | Koenigsberg et al. | 356/436 |
| 5,046,854 | 9/1991 | Weller et al. | 356/440 |
| 5,069,552 | 12/1991 | Cramer et al. | 356/436 |

*Primary Examiner*—Vincent P. McGraw
*Assistant Examiner*—LaCharles P. Keesee, II
*Attorney, Agent, or Firm*—Leonard A. Alkov; Wanda K. Denson-Low

[57] ABSTRACT

The sensor system monitors solutes in a liquid stream by analyzing the amount of light absorbed in a liquid in a particular wavelength band. The sensor system is arranged for selectability of the type of fiber used for transmission and adjustability of the liquid gap length in the liquid so that individual installations can be arranged with optimum characteristics for sensing particular chemical species in solution by absorption spectroscopy.

12 Claims, 3 Drawing Sheets

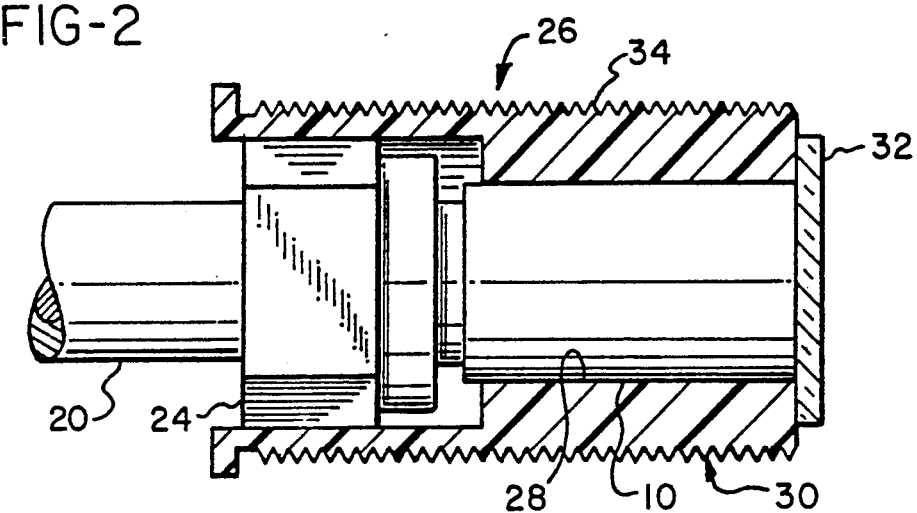
FIG-2
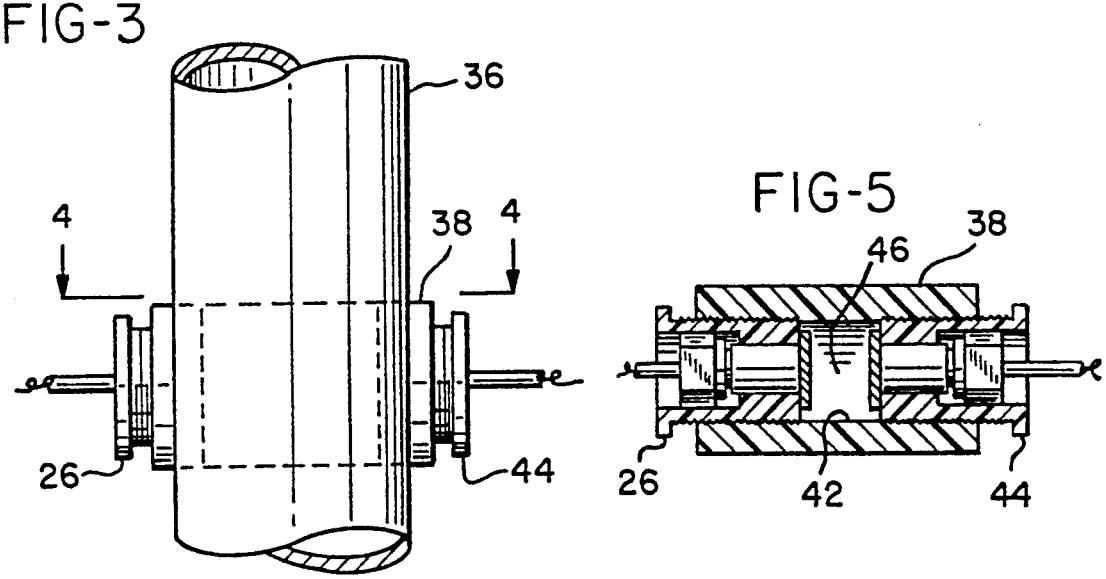
FIG-3
FIG-5
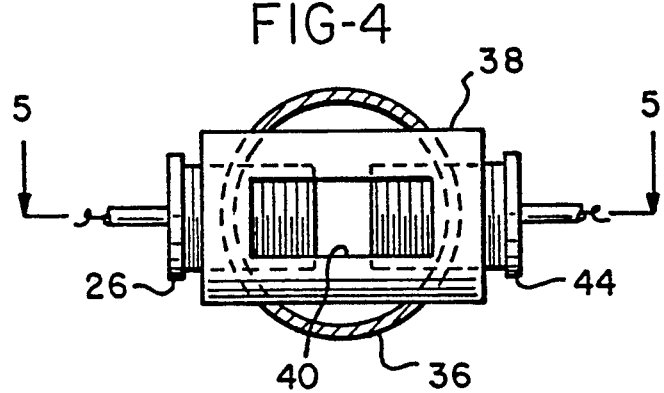
FIG-4

SENSOR FOR MONITORING SOLUTE IN A LIQUID STREAM

This is a continuation of application Ser. No. 07/785,727, filed Oct. 31, 1991, now abandoned.

FIELD OF THE INVENTION

This invention is directed to a sensor which monitors solutes by analyzing the amount of light absorbed in a liquid in a particular wavelength band. The sensor system is arranged for selectability of the type of fiber used for transmission and adjustability of the liquid gap length in the liquid so that individual installations can be arranged with optimum characteristics for sensing particular chemical species in solution by absorption spectroscopy.

BACKGROUND OF THE INVENTION

The apparatus and method described in Pesavento and Strawbridge U.S. Pat. No. 4,085,685 teach the manner in which absorption spectroscopy can be successfully used in the testing of chemical solutions, and particularly in electroplating solutions. Koenigsberg and O'Neal describe, in U.S. Pat. No. 4,989,942, a useful structure for creating the light gap for positioning in the liquid solution. In this case, reliability is stressed by protection of the components against the adverse electroplating environment.

Different solutes may have spectroscopic peaks at different wavelengths. It is this characteristic which permits identification of a particular solute. However, these wavelengths may be best served by different light sources, and these different light sources may be best transmitted through different types of optical fibers. Furthermore, the peaks may be best detected at different detector gaps. As a result, for a sensor system to have a fairly wide utility, it is necessary to be able to adjust the light gap, as a function of concentration and transparency of the liquid stream, change light sources and/or filters to provide light in the proper wavelength band for which the solute is being, and to be able to change the optical fiber to one which is most suitable for the particular wavelength band. The sensitivity of the system is determined by its optical path length across the gap through which the stream passes. An increase in path length yields greater sensitivity: greater differentiation of lower concentrations. However, with a greater path length and corresponding increased light absorption, the amount of light reaching the detector may drop below the limit for accurate measurement. A variable path length allows the system to be adjusted for maximum sensitivity within the operating range of the detector. Thus, there is a need for providing a sensor and system with an adjustable, selectable path length. Fiber optic cables come in different types, each with its spectral window of maximum transmittance, depending on the material used in the optical fiber. If a sensor is to be used at different wavelengths, it is also necessary to change the fiber. Thus, changing the fiber optic cable to a different material is also necessary to provide wide utilization of the sensor. A sensor with interchangeable cables is not limited to any one cable and its corresponding spectral range, but such a sensor can use any fiber optic cable.

SUMMARY OF THE INVENTION

In order to aid in the understanding of this invention, it can be stated in essentially summary form that it is directed to a sensor for monitoring solutes in a liquid stream, together with its associated system. The sensor has an adjustable path length and has fiber optic cables detachably attached thereto so that an appropriate cable for the wavelength of the solute of interest can be attached to the sensor.

It is thus a purpose and advantage of this invention to provide a sensor for monitoring solutes in a liquid stream wherein the sensor and its system are arranged for the sensing of different solutes, which may require different fiber optic cables and/or different gap length.

It is another purpose and advantage of this invention to provide a system and its sensor for monitoring solutes wherein the sensor and system are selectable so as to be sensitive to the selected solute.

It is a further purpose and advantage of this invention to provide a sensor and sensor system wherein the fiber optic cables are of substantially standard nature, together with standard connectors so that different selected standard cables can be employed depending on the wavelength of interest in the spectroscopic analysis.

Other purposes and advantages of this invention will become apparent from a study of the following portion of the specification, the claims and the attached drawings wherein:

BRIEF DESCRIPTION OF THE DRAWINGS

FIG. 2 is an enlarged side-elevational view of a sensor element, with parts broken away and parts taken in section.

FIG. 3 is a side-elevational view of a tube carrying a liquid stream, with the sensor of this invention mounted in the tube.

FIG. 4 is a downward-looking view of the sensor, as seen generally along line 4—4 of FIG. 3.

FIG. 5 is a section through the sensor, seen generally along line 5—5 of FIG. 4.

DESCRIPTION OF THE PREFERRED EMBODIMENTS

Figure 6:
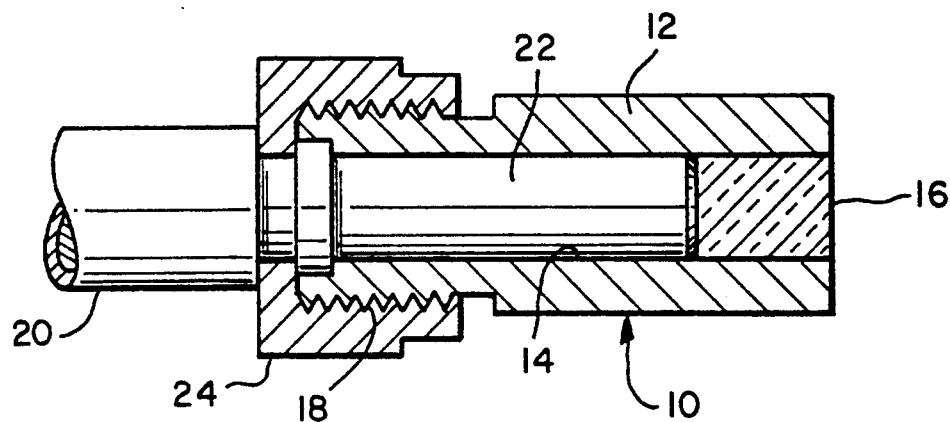
FIG. 6 is a side-elevational view, with parts broken away and parts taken in section of the lens assembly and showing how the lens assembly attaches to a fiber optic cable.

FIG. 6 illustrates a lens assembly 10 which comprises a body 12, which contains a recess 14. The forward end of the recess 14 has sealed therein a GRIN lens 16. The rear end of the lens assembly has external threads 18 thereon. Fiber optic cable 20 comprises a sheath and end termination on a clad fiber. The end termination includes rod 22 with transparent core which extends into the recess 14. Rod 22 carries nut 24 which engages on threads 18 and holds the rod 22 in its recess with its tip against the GRIN lens 16. The cable 20 may be removed and replaced with a cable of a different length or different optical properties.

The lens assembly 10 is inserted into sensor element 26. The sensor element 26 has an interior recess 28 into which the lens assembly is inserted, see FIG. 2. The recess extends all the way through the sensor element body 30 and is closed at the sensor end by means of window 32. The lens assembly 10 is metallic with the GRIN lens 16 in its recess, and these are not suitable materials for use in most plating bath environments. Therefore, the body 30 is made of synthetic polymer composition material, which is resistant to plating bath materials. The window 32 is also resistant to the plating bath materials and is of a suitable material to be substantially transparent to the wavelength of interest Sensor element 26 has threads 34 on the exterior thereof. These threads are for the purpose of adjusting the position of the sensor element 26 and the position of lens assembly 10.

Figure 1:
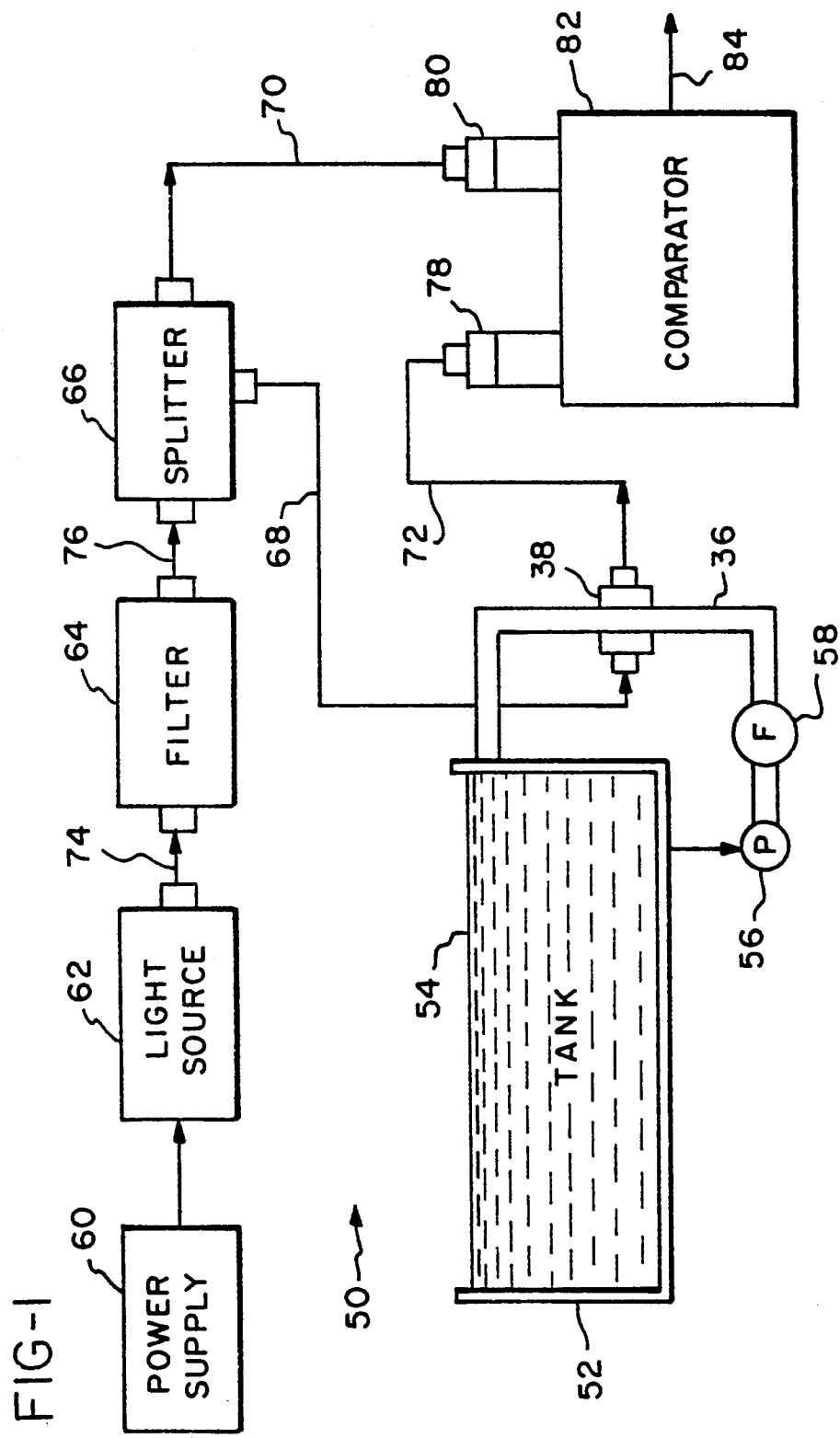
FIG. 1 is a schematic diagram of the system which employs the sensor of this invention.

FIGS. 1, 2 and 4 show tube 36 through which flows the liquid which contains as a solute an ion of interest which the sensor of this invention will monitor by absorption spectroscopy. Sensor carrier 38 is a tube which is mounted transversely of the liquid stream tube 36. Sensor carrier 38 has an opening 40 therethrough which is in line with the opening in the liquid tube 36 so that the opening 40 passes the liquid. There may be an opening in tube 36 around the sensor carrier 38. The sensor carrier has a threaded opening 42 therethrough. The threaded opening 42 intersects the fluid opening 40. The threaded opening 42 is open at both ends of the sensor carrier, and the threads are the same as the exterior threads 34 on the sensor element 26. As is seen in FIGS. 3, 4 and 5, the sensor element 26 is threaded into one end of the sensor carrier. Another sensor element 44, identical to the sensor element 26, is threaded into the other end of sensor carrier 38. The distance between the windows on the two sensor element 26 and 44 is the sensor gap through which the liquid flows. The structure is arranged so that the sensor gap can be selected by adjustment of the sensor elements 26 and 44 being threaded into and out of the sensor carrier. In this way, the sensor gap can be precisely selected.

FIG. 1 shows a sensor system 50 which incorporates the sensors described above. Tank 52 contains liquid solution 54. The liquid is drawn from the bottom of the tank by pump 56, which delivers the liquid through filter 58, and the liquid then passes through line 36 back to the tank. It is this liquid which is to be sensed by the sensor system 50. The liquid may be a plating solution or other solution. For the most part, the liquid will be a water solution. Plating solutions include acid copper plating baths, acid solder, acid nickel, alkaline electroless copper plating bath, and center-feed baths with special additives.

Electric power supply 60 powers light source 62. The light source 62 may be a broad spectrum light source or a narrow spectrum source such as a laser. In the case of a laser, its frequency must be in the absorption band of the material of interest in the analysis. In the case of a broad band light source, the light is delivered to filter 64, which narrows the band width to the absorption area of interest. In some installations there are two filters. Instead of a filter connected between lines 74 and 76, there would be a filter connected between line 72 and photodiode 78 and another filter connected between line 70 and photodiode 80. The light passing the filter 64 is delivered to splitter 66. The purpose of the splitter system is to provide a light source reference signal. A stable light source would eliminate the need for a reference signal. The splitter 66 delivers a major part of the light energy through line 68 and a minor part through line 70. The split may be 80 percent 20 percent, for example. Line 68 is connected between splitter 66 and sensor element 26, while line 72 is connected between sensor element 44 and the comparator. Line 74 connects the light source to the filter, and line 76 connects the filter to the splitter. Each of the lines 68-76 is a standard fiber optic line having a standard connector thereon of the type illustrated in FIG. 6. Thus, these lines may be changed in accordance with the transmission capability at the wavelength of interest. Furthermore, these lines can be changed for lines of different length for different installations. The changeability of the lines, both for purposes of length and wavelength transmissibility provides a considerable latitude of operation for the sensor carrier 38 and the system 50. Line 70 brings in a reference signal from the splitter, and line 72 brings in the light transmitted through the gap between the pair of sensor elements in sensor carrier 38. The distance between the sensor elements is also adjustable to provide maximum sensitivity for the compound of interest. The photodiodes 78 and 80 are mounted on comparator 82, which compares the signal intensity in the two input lines 70 and 72 at the wavelength of interest. The photodiodes 78 and 80 are provided to convert the optical signal into an electric current in each of the inputs into the comparator. The comparator compares the signal strengths so that the output 84 signals the concentration of the compound of interest. The following examples illustrate the manner in which the sensor system of this invention is widely applicable for testing for concentrations of various compounds of interest.

EXAMPLE 1

The liquid solution 54 in the tank is on electroless copper plating solution. Among other things, it contains the copper ion which has an absorption band at 684 nanometers. The light source 62 is a white light source, while filter 64 has a significant band path in the band range from 650 to 800 nanometers. The concentration of copper ions in the solution 54 is approximately 4 grams per liter. At this concentration, the spacing between the sensor elements 26 and 44 is approximately 18 centimeters. The lines 68-76 are chosen to have a band path at the selected absorption peak wavelength and, thus, are made of pure fused silica. With this arrangement, the comparator 82 can signal in real time the concentration of the copper ion in solution 54 between 3 and 5 Gm/L.

EXAMPLE 2

The liquid solution 54 in the tank is a centerfeed bath (high and low deposition electroless copper). Among other things, it contains the copper ion which has an absorption band at 735 nanometers. The light source 62 is a white light source, while filter 64 has a significant band path in the band range from 700 to 800 nanometers. When the concentration of copper ion in the solution 54 is approximately 2.55 grams per liter, the spacing between the sensor elements 26 and 44 is approximately 18 centimeters. The lines 68-76 are chosen to have a band path at the selected absorption peak wavelength and, thus, are made of pure fused silica. With this arrangement, the comparator 82 can signal in real time the concentration of the copper ion in solution 54 between 1.5 and 3.6 grams per liter.

EXAMPLE 2

The liquid solution 54 in the tank is a solder-plating solution. Among other things, it contains peptone which is a key organic additive in the solder plating tank and serves as a plating grain definer. The peptone has an absorption band at 330 nanometers. The light source 62 is a white light source, while filter 64 has a significant band path in the band range from 250 to 350 nanometers. The concentration of peptone in the solution 54 is approximately 2.5 grams per liter. At this concentration, the spacing between the sensor elements 26 and 44 is approximately 18 centimeters. The lines 68-76 are chosen to have a band path at the selected absorption peak wavelength and, thus, are made of U.V. enhanced fused silica. With this arrangement, the comparator 82 can signal in real time the concentration of the peptone in solution 54 between 1 and 4 Gm/L.

Figure 7:
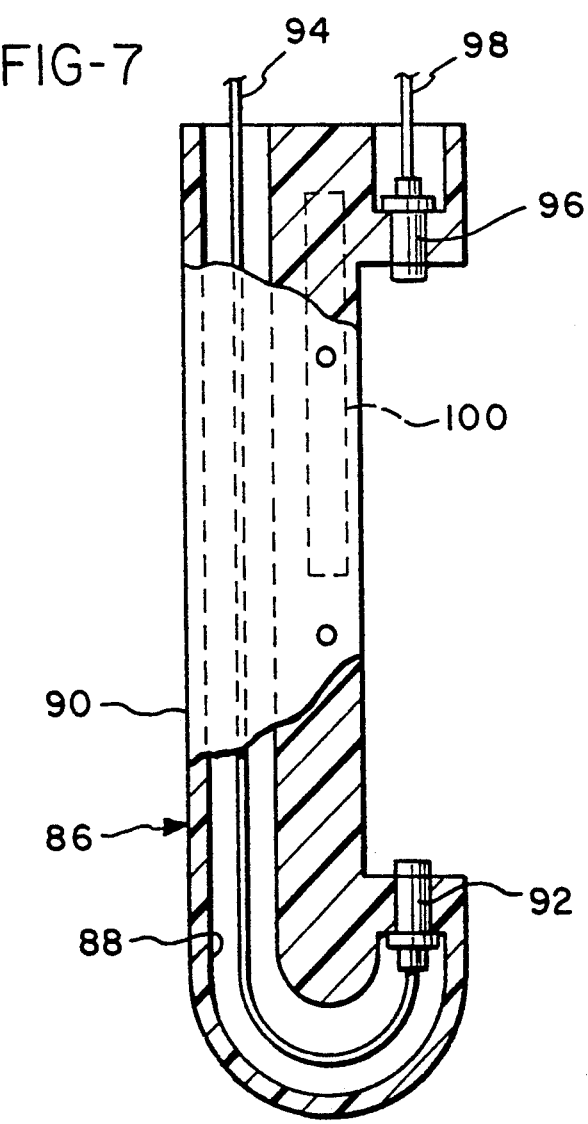
FIG. 7 is a side-elevational view, with parts broken away and parts taken in section, showing an embodiment of the sensor in accordance with this invention sized to test for a particular species of solute.

The above examples represent experimental results with the larger gap sensor of FIG. 7. With higher concentrations of species being evaluated, it is thought that a shorter gap length in the sensor will provide useful concentration information. The following examples represent anticipated data.

EXAMPLE 4

The liquid solution 54 in the tank is on electrolytic copper plating solution. Among other things, it contains the copper ion which has an absorption band at 830 nanometers. The light source 62 is a white light source, while filter 64 has a significant band path in the band range from 650 to 800 nanometers. When the concentration of copper ions in the solution 54 is approximately 75 grams per liter, the spacing between the sensor elements 26 and 44 is approximately 1 centimeter. The lines 68-76 are chosen to have a band path at the selected absorption peak wavelength and, thus, are made of pure fused silica. With this arrangement, the comparator 82 can signal in real time the concentration of the copper ion in solution 54 between 60 and 90 Gm/L.

EXAMPLE 5

The liquid solution 54 in the tank is a solder-plating solution. Among other things, it contains peptone which is a key organic additive in the solder plating tank and serves as a plating grain definer. The peptone has an absorption band at 330 nanometers. The light source 62 is a white light source, while filter 64 has a significant band path in the band range from 250 to 350 nanometers. When the concentration of peptone in the solution 54 is approximately 2.5 grams per liter, the spacing between the sensor elements 26 and 44 is approximately 1 centimeter. The lines 68-76 are chosen to have a band path at the selected absorption peak wavelength and, thus, are made of U.V. enhanced fused silica. With this arrangement, the comparator 82 can signal in real time the concentration of the peptone in solution 54 between 1 and 4 Gm/L.

EXAMPLE 6

The task is to provide a monitoring system for a chemical bath containing copper with a concentration range of 60 to 90 grams per liter. A spectral scan is taken of the solution at different copper concentrations. This will identify the spectral absorption band for the copper in the solution. For copper, it is known, but it is necessary to check for interfering bands from other constituents in the bath. Once an isolated copper absorption band has been identified, a fiber optic cable is chosen that has a strong transmission band which includes the copper absorption band. In this example, the working band is 650 to 850 nanometers.

When building a system, three main areas need to be specified: the light source; the light transferring medium, i.e., the cable; and the light detector. The cables have been determined above. The light source must be chosen on the basis of its emission spectrum. It must have a strong band including the working band of the system. The one chosen for this example is a Xenon arc lamp.

The light detector chosen must be sensitive in the working band. For this example, Germanium was chosen. The equipment that uses this detector can measure the light intensity down to −60 decibels. However, the accuracy starts to drop when the level drops below −45 decibels. This means that the system should be designed so that the light intensity will not drop below −45 decibels.

The copper solution of interest varies in concentration from 60 to 90 grams per liter. The user wishes to establish control limits of 65 to 80 grams per liter. It is, thus, unlikely that the concentration will be as high as 90. Ninety is thus chosen as the upper test limit.

The path length of the optrode can now be determined. The greater the path length, the more accurate the optrode. However, as the path length gets longer, the amount of light and thus the decibel reading gets lower. A test solution of 90 grams per liter copper is prepared. Ninety is chosen because it absorbs the most light per centimeter path length of any solution in the concentration range. The optrode is placed in the solution. As the path length is increased, the power level will drop. The path length is increased until the power level drops to around −45 decibels. The path length at that point is the optimum path length. With this information determined, the system is then built, installed and calibrated.

The differences in gap length between the sensor elements 26 and 44 show that different gap lengths are desirable for different solutions. FIG. 7 illustrates a structure wherein a larger gap length can be provided. Sensor body 86 is J-shaped and has a J-shaped channel 88 cut therein. Cover 90 is broken away in FIG. 7 to show the channel. Sensor element 92 is the same as sensor element 26. Sensor element 92 is positioned to be upwardly facing on the J-shaped sensor body and is secured therein. It has a window thereover the same as window 32 to protect the sensor element. Line 94 is connected to the sensor element in the same way as illustrated in FIG. 2 and extends upward out of the sensor body. Sensor element 96 is also the same as sensor element 26 and is positioned to face the sensor element 92 with a known gap therebetween. Line 98 is connected to sensor element 96. Lines 94 and 98 correspond to lines 68 and 72 in FIG. 1. The sensor body 86 with its sensor element is used in place of the sensor carrier 38 in FIG. 1. Instead of placing the sensor body 86 in the flow lines of the tank 52, it is hooked over the edge of the tank so that both of the sensor elements are submerged. Clip 100, shown in dashed lines in FIG. 7, permits attachment of the sensor 86 to the side of the tank. Of course, lines 94 and 98 are fiber optic lines with standard connectors thereon so as to permit changes in fiber for different absorption peaks to be sensed and different fibers for different lengths of installation between the tank and the sensor system 50. The sensor 86 provides a longer gap length than is possible for the sensor 38, and an example of its use follows.

From this description it can be seen that the invention includes a selection between a fixed path length sensor and a variable path length sensor. Furthermore, the sensor is remote from the sensor system by means of fiber optic cables. The cables are selectable for transmission band width and selectable length in accordance with installation requirements. Interchangeable fiber optic cables permit monitoring low levels of organic and inorganic solutes in the ultraviolet, visible and near-infrared region. In accordance with absorption spectroscopy, the solute of interest absorbs light at a given wavelength. The higher the concentration in the solvent, the more light is absorbed. By monitoring the intensity of the light at the wavelength of the absorption peak, after the light passes through the sample, the concentration can be determined. The light source 62 emits light which contains, but is not necessarily limited to the wavelength that the chemical species of interest will absorb. The light source must be stable, and this is usually accomplished with a Xenon arc lamp, but could be accomplished with a laser diode, laser or other light source. The light is detected at the comparator, by photodiodes 78 and 80. The photodiodes convert the light to the electric current which is compared in comparator 82.

The sensors 38 and 86 provide a gap or path length through which the light must pass before it reaches the detector. The sample is in the gap, and this is where the light absorption takes place. The size of the gap affects the amount of light absorbed. If too much light is absorbed, not enough light will reach the detector for accurate measurement. The variable path length sensor 38 allows the amount of light absorption to be optimized for maximum sensitivity, but in the detector's operating range.

In testing the sensor system, appropriate calibration solutions are placed in the sensor such that the solution sees the entire path length for light absorption by the chemical. The fiber optic cables from the sensor are attached to the light source and the comparator, as shown in FIG. 1. The comparator is interfaced with a computer for real-time monitoring of the chemical of interest. Light absorption numbers produced by the comparator for known chemicals in the ultraviolet visible region are expressed electrically by the comparator. These light absorption values are plotted against the concentrations of chemicals which yielded linear plots following Beer-Lambert law, depending on the concentration regions. The Beer-Lambert law can be expressed by the equation:

$$A = \log_{10} I_o/I = Ecb$$

where:
A = absorbance
$I_o$ = the intensity of the incident light
I = the intensity of the transmitted light
E = the molar absorptivity at a given wavelength and temperature
c = the concentration (molarity)
b = the path length Test results have revealed that there are different regions of linearity in Beer-Lambert plots and that the entire range of concentrations from the parts per million level to the percentage level will not offer linear graphs when plotted against light absorption. Values of the slope and intercepts from the linear plots were computed to express the real-time concentration of the chemical of interest. Repeatability tests were performed by using the calibration solution several times to establish the confidence level. In this way, a sensor system for monitoring solutes of various times and various concentrations in liquid is provided.

This invention having been described in its presently contemplated best mode, it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An optical sensor for monitoring solutes in a liquid stream comprising:

a sensor carrier having a sensor axis, a sensor opening in said sensor carrier, said sensor opening lying on said sensor axis, said sensor opening having threads of substantially uniform diameter in said sensor carrier and defining said sensor opening, said screw threads lying about said sensor axis, a liquid opening through said sensor carrier so that liquid can pass therethrough, said liquid opening intersecting with said sensor carrier axis;

first and second sensor bodies mounted within said sensor opening in said sensor carrier, each of said sensor bodies having threads of uniform diameter thereon, both of said sensor bodies being engaged in said threads in said sensor opening in said sensor carrier, each of said sensor bodies having a recess therein and a window on said recess, said first and second sensor bodies being positioned within said sensor carrier so that said windows face each other and define a liquid gap therebetween, said sensor bodies being threadedly engaged in said sensor carrier so that they are axially adjustable within said sensor carrier on said threads within said sensor carrier so as to provide adjustment for said gap between said windows, each of said sensor bodies extending out of said sensor carrier for accessibility to said sensor bodies for adjustment thereof with respect to said sensor carrier so that said first and second bodies are adjustable along said axis to adjust the gap therebetween;

first and second lens assemblies respectively mounted in said recesses in said first and second sensor bodies, each of said first and second lens assemblies having means thereon for detachable connection of a fiber optic cable thereto, each of said lens assemblies comprising a body having a recess therein and an opening therethrough, said body having a face with said opening extending through said face, a lens in said opening adjacent said face, said opening being sized to receive the rod on a fiber optic cable end termination and said body having external threads thereon to be engaged by a nut on a fiber optical cable end termination so that the fiber optic cable can be attached to said body and the rod on said cable positioned within said recess in said body and against said lens in said recess so that said first and second lens assemblies being respectively retained within said first and second sensor elements and said first and second sensor elements being threadedly engaged within said sensor carrier so that said lens assemblies lie on said axis and lie in a position so that they face each other to define a fluid gap between said windows with both said first and second lens assemblies lying on the same optical axis so that light from one of said lens assemblies passes across the gap and impinges on the other of said lens assemblies and some of the light is absorbed in the fluid in said gap and the fluid gap length can be adjusted by threaded engagement of said sensor elements within said sensor carrier to optimize absorption in accordance with the fluid in said gap.

2. The sensor of claim 1 wherein said lens in each said lens assembly is a GRIN lens in said body to focus light between an optical fiber attached to said body and the gap.

3. The sensor of claim 1 wherein said sensor carrier is J-shaped.

4. An optical sensor for detecting the concentration of a particular material in solution by absorption spectroscopy comprising:
 a light source providing light at an absorption peak of the material in solution, said light source being connected to a beam splitter which provides first and second light beams of proportional intensity;
 a comparator having first and second photodetectors, said second beam being connected to said second photodetector;
 a sensor carrier made of synthetic polymer composition material, a sensor opening in said sensor carrier, said sensor opening defining a sensor axis, said sensor opening having screw threads thereon around said sensor axis, a liquid passage through said sensor carrier and intersecting said sensor axis;
 first and second sensor bodies mounted within said sensor opening in said sensor carrier, said first and second sensor bodies each being threaded on the exterior thereof so that they are in threaded engagement with said threaded sensor opening in said sensor carrier so that said first and second bodies are adjustable along said axis to adjust the gap therebetween, said sensor bodies being made of synthetic polymer composition material, each of said sensor bodies having a recess therein extending along said axis, a window on each of said sensor bodies closing one end of said opening therein, said windows being adjacent each other to define the gap therebetween;
 first and second lens assemblies respectively mounted in said recesses in said first and second sensor bodies, each of said first and second lens assemblies being made of metallic material and having a recess therethrough, a lens in each said lens assembly body to close one end of said recess, external screw threads on the other end of said lens assembly body for detachable connection of a fiber optic cable thereto, said sensor carrier being configured to hold said first and second lens assemblies in a position so that they face each other on said axis to define a fluid gap therebetween with both said first and second lens assemblies lying on the same optical axis so that light from one of said lens assemblies passes across the gap and impinges on the other of said lens assemblies and some of the light is absorbed in the fluid in said gap and the fluid gap length can be adjusted in accordance with the fluid in said gap, said first beam being connected to said first sensor body and said second sensor body is connected to said first photodetector, each of said connections between said light source, said splitter, said sensor and said first and second photodetectors being by disconnectable, interchangeable fiber optic connectors.

5. The system of claim 4 wherein said fiber optic connectors between said splitter, said sensor and said photodetectors have connectors thereon for disconnectable connection to said splitter, said sensor and said photodetectors so that fiber optic cables of different length and built to carry different light wavelengths can be installed in accordance with the fluid in said gap.

6. The system of claim 5 wherein said sensor body is J-shaped.

7. The sensor system of claim 6 wherein said J-shaped body is made of material resistant to the fluid which contains the material being detected and said J-shaped body has a channel therein to receive on e of the fiber optic cables and a cover over said channel to protect the cable, said cover being removable to permit changing of the cable.

8. The sensor system of claim 7 wherein said lens assembly in said sensor element has attachment means thereon for detachable attachment of the fiber optic cable and has a GRIN lens therein so as to focus light from the fiber optic cable across the gap.

9. The sensor system of claim 8 wherein said lens assembly has screw threads thereon for screw thread attachment of a standard fiber optic cable for cable selection in accordance with the type of fluid in said gap and has an optical rod therein coupling the cable to said GRIN lens.

10. The sensor system of claim 7 said sensor element has a lens assembly therein and has a window thereon, said window being substantially transmissive to the wavelength of interest and protecting said lens assembly from the fluid in the gap.

11. The sensor system of claim 10 wherein said lens assembly in said sensor element has attachment means thereon for detachable attachment of the fiber optic cable and has a GRIN lens therein so as to focus light from the fiber optic cable across the gap.

12. The sensor system of claim 11 wherein said lens assembly has screw threads thereon for screw thread attachment of a standard fiber optic cable and has an optical rod therein coupling the cable to said GRIN lens.

* * * * *